United States Patent [19]

Wakarchuk

[11] Patent Number: 5,750,129
[45] Date of Patent: May 12, 1998

[54] COMPOSITE POLYMER MATRICES FOR CONTROLLED RELEASE OF SEMIOCHEMICALS

[75] Inventor: David A. Wakarchuk, Burnaby, Canada

[73] Assignee: Phero Tech Inc., Delta, Canada

[21] Appl. No.: 686,471

[22] Filed: Jul. 25, 1996

Related U.S. Application Data

[63] Continuation-in-part of Ser. No. 242,021, May 5, 1994, abandoned, which is a continuation-in-part of Ser. No. 937,469, Aug. 28, 1992, abandoned.

[51] Int. Cl.$^6$ .................................................. A01N 25/08
[52] U.S. Cl. .................... 424/408; 424/406; 424/409; 424/410; 424/411; 424/486; 424/84; 514/919
[58] Field of Search ................................. 424/408, 406, 424/405, 409–411, 486, 84; 514/919

[56] References Cited

U.S. PATENT DOCUMENTS

| | | | |
|---|---|---|---|
| 4,017,030 | 4/1977 | Coplan et al. | 239/44 |
| 4,323,556 | 4/1982 | Dal Moro et al. | 424/84 |
| 4,325,941 | 4/1982 | Dal Moro et al. | 424/84 |
| 4,445,641 | 5/1984 | Baker et al. | 239/6 |
| 4,594,380 | 6/1986 | Chapin et al. | 524/144 |
| 4,639,393 | 1/1987 | Van Kohorn et al. | 428/304.4 |
| 4,715,536 | 12/1987 | Capizzi et al. | 239/54 |
| 4,793,555 | 12/1988 | Lee et al. | 239/6 |
| 4,891,388 | 1/1990 | Graiver et al. | 521/64 |
| 4,908,208 | 3/1990 | Lee et al. | 424/409 |
| 4,923,119 | 5/1990 | Yamamoto et al. | 239/55 |
| 4,979,673 | 12/1990 | Wilk | 239/6 |
| 5,008,115 | 4/1991 | Lee et al. | 424/486 |
| 5,069,231 | 12/1991 | Rutherford | 131/335 |

FOREIGN PATENT DOCUMENTS

| | | |
|---|---|---|
| 8490 | 6/1989 | Czech Rep. |
| 2945655 | 5/1981 | Germany |
| 3524180 | 1/1986 | Germany |

OTHER PUBLICATIONS

Kydonieur Ed. Insect Suppresssion: vol. I–CRC 1982 pp. 214,217,219,220,224,225,227,228,255.

Fitzgerald, T.D. et al., 1973: Environmental Entomology, vol. 2, #4, pp. 607–610.

Kim, J. et al., 1988: Appl. Radiat. Isot., vol. 39, #11, pp. 1145–1152.

Smit, C.N. et al., 1991: Intern. Symp. Control Rel. Bioact. Mater., Controlled Release Society, Inc. pp. 81–82.

Weatherston, I., et al., 1985: Journal of Chemical Ecology, vol. 11, #8, pp. 953–965, pp. 967–978.

Zeoli, L.T., et al., 1982: "Controlled Release Technologies" in Insect Suppression with Controlled Release Pheromone Systems, vol. 1, ed. G. Zweig, CRC Press Inc., Boca Raton, FL. pp. 131–144.

*Primary Examiner*—Neil S. Levy
*Attorney, Agent, or Firm*—Oyen Wiggs Green & Mutala

[57] ABSTRACT

Composite polymer dispensers capable of controlled release of semiochemicals have been developed. The dispensers make use of a solid elastomer matrix reservoir which is at least partially surrounded by a permeable release rate controlling polymer membrane. The matrix materials are polyurethanes compatible with many types of semiochemicals and additives. The release rates of semiochemicals from the dispensers can be varied over a wide range by manipulation of the reservoir conditions and by selection of the type of permeable polymer membrane surrounding the device. The dispensers can have a variety of forms and can be produced by a simple process. The semiochemical devices produced by this method are useful for managing insect and other pests through attraction to traps, for population monitoring or for mass trapping. The devices may also be used to dispense anti-aggregation pheromones or repellents in addition to use for mating confusion or disruption.

7 Claims, 3 Drawing Sheets

COMPOSITE POLYMER MATRICES FOR CONTROLLED RELEASE OF SEMIOCHEMICALS

This application is a continuation-in-part of application Ser. No. 08/242,021 filed May 5, 1994 now abandoned, which in turn was a continuation-in-part of application Ser. No. 07/937,469 filed Aug. 28, 1992 which has been abandoned.

FIELD OF THE INVENTION

This invention pertains to novel and versatile devices for use as semiochemical controlled release dispensers. More particularly, hydroxy-terminated polybutadiene resins, or other polyols, can be combined with semiochemicals, additives, and an isocyanate component to produce a solid phase reservoir surrounded at least partially by a permeable, release rate controlling polymer membrane.

BACKGROUND OF THE INVENTION

Semiochemicals are an extremely diverse group of chemicals encompassing many functional groups and having at least several hundred members. "Law and Regnier (1971) proposed the term 'semiochemicals' (Gk. semeon, a mark or signal) for chemicals that mediate interactions between living organisms" taken from (Norlund et al. 1981). This definition is well known well known and has been in common usage by persons skilled in the art for many years.

Semiochemicals transmit signals to members of the same species as well as different species. These chemicals have been identified in many organisms including bacteria, yeast, plants, insects and animals. The U.S. Environmental Protection Agency which regulates certain pest control uses of semiochemicals has used a slightly narrower definition: "Chemicals emitted by plants or animals that modify the behaviour of receptor organisms of like or different kinds are semiochemicals." (1982 Pesticide Assessment Guidelines, Subdivision M, Biorational Pesticides [NTIS publication PB-83153965 page 2]). Often semiochemicals are not emitted as a pure chemical, but rather as a blend of several compounds. The most studied semiochemicals are the pheromones, which transmit chemical signals within the same species (The Merck Index 11th ed. 1989) and have been identified in at least 1,600 species (Mayer and Mclaughlin 1990, Arn et al. 1992). Kairomones, allomones and synomones are other types of semiochemicals that are intra species signals (Norlund et al. 1981). Allomones are compounds that serve to benefit the emitting species, while kairomones benefit the perceiving species. Synomones are chemical signals which serve to benefit both the emitting and perceiving species. It is worth note that the terms pheromone, allomone and kairomone are not mutually exclusive. For example, a semiochemical may be a pheromone in one species while the same chemical acts as a kairomone for predators of that species.

The use of semiochemicals as a tools in integrated pest management (IPM) is increasing. Uses for semiochemicals have been found in forestry, agriculture and urban industrial locations (Mitchell 1981, Ridgeway et al. 1990). Other compounds of use in integrated pest management also include synthetic chemicals not found naturally (unnatural chemicals) that mimic the biological actions of semiochemicals, for example the "male lures" of terphritid fruit flies (Cunningham et al. 1990). The chemical mixture known as "trimedlure" (t-butyl esters of 4- and 5-chloro-2-methylcyclohexan-1-carboxylic acid) is a secific illustration.

The Mediterranean fruit fly, *Ceratitis capitata*, does not produce these chemicals, nor are they found in nature. However, females of this species respond to this mixture as if it were a male produce sex pheromone. Thus trimedlure is an unnatural synthetic behaviour-modifying chemical that mimics the the function of a semiochemical (sex pheromone). These synthetically prepared, unnatural chemicals that cause behavoiral responses that copy or mimic the actions of semiochemicals are herein defined as an unnatural synthetic behaviour-modifying chemicals and are functionally equivalent to their corresponding semiochemicals. A skilled practitioner will be aware that chemicals such as pesticides, fungicides, bactericides, insecticides, nematocides, acaricides, molluscicides and growth regulators are not semiochemicals, nor are they semiochemical mimics.

In contrast to pesticides, semiochemicals do not work through toxic action and in general are of low toxicity to non-target species (Ridgeway et al. 1992). Pesticides tend to be broad spectrum in the organisms affected while semiochemicals are much more specific, affecting at most a few species. Semiochemicals can often replace or substantially reduce the amount of pesticide needed for pest control applications. Semiochemical use in pest management may include strategies such as population monitoring, quarantine trapping, mass trapping, barrier trapping, and mating disruption. The use of anti-aggregation pheromones, alarm pheromones, anti-feedants, oviposition deterrents, pollination enhancement and other types of behaviour modifications are known.

The widespread use of semiochemicals in pest control applications has been limited partly by difficulties encountered in controlled delivery of the chemicals to the environment. Semiochemical-based pest management relies to a large extent on precise slow release device technology for its successful implementation. For example, the use of insect pheromones to lure pests to traps used for population monitoring requires a very specific delivery rate. Too low a delivery rate may be below the threshold of perceptions while too high a delivery rate may confuse or repel the insect and prevent the insect from entering the trap. In other applications such as mating disruption, too low a release rate or premature exhaustion of slow release devices can severely reduce the efficacy of the treatment, while too high a release rate or too long a lifespan of devices loaded with an expensive semiochemical may make the cost of treatments prohibitive. Zeoli et al. (1982) have summarized controlled release technologies used for delivering semiochemicals and have categorized the dispensers types into four groups: monolithic systems, laminated structures, reservoir systems without rate controlling membranes and reservoir systems with rate controlling membranes.

1. Monolithic systems

These one material systems consist of inert polymeric matrices impregnated with the semiochemical as the active ingredient (AI). Such homogenous devices are simple and they lend themselves to a number of applications. However, the release characteristics depend largely on the shape of the device, and the capacity of the polymer to hold the semiochemical, both of which may limit the longevity of the device. Release of AI from monolithic devices tends to be logarithmic over time with much of the active agent being lost in the early part of the device lifespan. The most constant release from this type of device usually occurrs when the reservoir is almost exhausted. Examples of this technology are polyvinylchloride (PVC) impregnated with semiochemical (Fitzgerald et al. 1973) or silicone rubber impregnated with fragrances as in U.S. Pat. No. 4,725,575 (Union Camp Co.), or silicone-urethane copolymers used as matrices for dispensing fragrances or pheromones as in U.S. Pat. Nos. 4,908,208 and 5,008115 (Dow Corning Co.), urethane matrices for dispensing pesticides as in U.S. Pat. No. 4,594,380 (AT&T Bell Laboratories) or acrylate polymers impregnated with pheromones (Smith et al. 1991 and Kim et al. 1988).

2. Laminated structures

These devices have relatively good release characteristics, approaching zero order (constant) release. However, the manufacture of these devices requires multiple processing to produce the laminate. An example of this technology are laminated dispensers described in U.S. Pat. No. 4,639,393 (Herculite Protective Fabrics), and German Patent No. 3,524,180 (Montedison S.p.A.).

3. Reservoir systems without rate controlling membranes

These can be exemplified by capillary release devices as described in U.S. Pat. No. 4,017,030 (Albany International Co.). These devices have been used despite undesirable high initial losses of semiochemical (Weatherston et al. 1985) and difficulty in handling.

4. Reservoir systems with a rate controlling membrane

Dispensers of this type generally provide near constant release characteristics which are governed by a permeable membrane. The membrane composition and surface area can be varied to effect changes in the release rates. Examples are described in U.S. Pat. No. 4,323,556 (Montedison S.p.A.), U.S. Pat. No. 4,445,641 (Bend Research Inc.), U.S. Pat. No. 4,979,673 (I. J. Wilk), U.S. Pat. No. 4,923,119 (Shin-Etsu Chemical Co.), U.S. Pat. No. 4,793,555 (Dow Corning Corp.) and German Patent No. 2,945,655 (Celamerck G.m.b.H.).

Polyurethane chemistry is well known in the plastics industry, however the use of these polymers in semiochemical slow release devices has been limited to silicone-urethane copolymers. The terminology used herein to describe the reactants and the reactive process to produce a polyurethane semiochemical reservoir conforms to the customary meanings as given in "Polyurethane Handbook" ed. G. Oertel, Hanser Publishers or "The ICI Polyurethanes Book", 2nd Edition, ed. G. Woods, published by ICI Polyurethanes and John Wiley & Sons. The term polyol refers to a molecule with at least two hydroxyl groups. Polymeric polyols usually contain other chemical functionalities and the most common types of polyols used in urethane manufacture are polyether polyols (hydroxy-terminated polyethers) and polyester polyols (hydroxy-terminated polyesters). Generally polymeric polyols are not pure compounds, but rather mixtures which are usually characterized by the average properties of the mixture. The isocyanates described herein are molecules which contain at least two isocyanate groups. The term MDI refers to diphenylmethane diisocyanate (predominately 4,4' isomer) which is commonly used in industry as mixtures of pure MDI and polymeric MDI. At the molecular level, polyurethane polymers may consist of soft block domains which consist of long chains with few crosslinks, an elastic structure and a low glass transition temperature, or hard block domains which consist of highly crosslinked chains, a rigid structure and a high glass transition temperature. Some polyurethanes may contain both hard and soft segments.

The terminology thermoplastic and thermoset plastic have meanings commonly accepted in the industry, thermoset plastics cannot be melted without decomposition and loss of original physical properties while thermoplastics may be readily melted and cast into molds without loss of original physical attributes.

SUMMARY OF THE INVENTION

The invention is directed to composite semiochemical release devices composed of a homogeneous polyurethane matrix containing a dissolved or dispersed active agent and an active agent permeable polymer membrane which at least partially surrounds the matrix. The polymer matrix is prepared from a reactive mixture comprising a polyol and an isocyanate cross linking agent reacted in the presence of unreactive semiochemicals and additives.

The term composite polymer device has been used herein to indicate that the devices are constructed from at least a binary combination of separate polymers, namely a homogeneous polyurethane core containing a semiochemical active ingredient and a semiochemical permeable, separate polymer membrane at least partially surrounding the polyurethane core.

The polyol may be selected from the group consisting of hydroxy-terminated polybutadiene resins, polyether polyols, polyester polyols and mixtures thereof. The isocyanate component may be selected from the group consisting of monomeric or polymeric diphenylmethane diisocyanates, toluene diisocyanates, isophorone diisocyanate and hexamethylene diisocyanate or mixtures thereof. Semiochemicals compatible with the reactive process may be selected from the functional groups including: alkanes, alkenes, aromatic hydrocarbons, ethers, esters, epoxides, aldehydes, ketones, lactones, nitriles, imines, tertiary amines, thioethers, sulfoxides, sulfones, disulfide compounds, thioesters, organohalides, and mixtures thereof. Semiochemicals not compatible or reactive with the matrix include the functional groups: alcohols, carboxylic acids, thiols, primary and secondary amines, and phenols.

The reaction mixture may include anti-oxidants, ultraviolet light absorbers, pigments, dyes, fillers, blowing agents, plasticizers, other resin modifying agents and mixtures thereof.

The reaction mixture is polymerized in a device at least partially surrounded by a polymer layer selected from the group consisting of: polyvinyl chloride (PVC), PVC/vinyl copolymers, low and high density polyethylene, polyethylene/vinyl copolymers, polyethylvinyl acetate and copolymers, polyethylene terpthalate and copolymers, polypropylene, polyamide, polyimide, polyurethane, polyvinylidene fluoride, fluorinated ethylene proplyene polymers, polytetrafluoroethylene, silicone rubber, butyl rubber, neoprene rubber, isoprene rubber, cellulose acetate and laminated (co-extruded) membrane types (e.g. PVC/ fluorinated ethylene propylene polymers, polyethylene/ ethylvinyl acetate, polyethylene/polyethylene terpthalate and the like). Different semiochemicals will have different permeabilities with respect to the membrane used and this provides versatility in attaining various desired release rate characteristics.

In a further embodiment, the reactive urethane mixture can be cast in a semiochemical permeable polymeric tube. The tubing containing the urethane mixture and the semiochemical can be used as long cylinders or cut into short cylinders which serve as semiochemical dispensers.

In a broad aspect, the invention is directed to a composite polymer semiochemical controlled release rate dispenser comprising: (a) a polyurethane reservoir formed from a reaction mixture of a polyol, a polymeric isocyanate and an unreactive semiochemical compatible with the polyol and isocyanate reaction mixture; and (b) a semiochemical permeable polymeric membrane that covers at least part of the reservoir, and which regulates the release of the semiochemical from the dispenser.

The invention in another aspect pertains to a composite polymer semiochemical controlled release dispenser comprising: (a) a polyurethane reservoir formed from a reaction mixture of (i) a polyol selected from the group consisting of hydroxy-terminated polybutadiene resins, hydroxy-terminated polyether resins and hydroxy-terminated polyester resins, (ii) an isocyanate component selected from the group consisting of monomeric or polymeric diphenylmethane diisocyanate, toluene diisocyanate, isophorone diisocyanate, hexamethylene diisocyanate and polymeric hexamethylene diisocyanate, (iii) an unreactive semiochemical (s) having functional groups selected selected from the group consisting of alkanes, alkenes, alkynes, aromatic hydrocarbons, ethers, esters, epoxides, aldehydes, ketones, lactones, nitriles, imines, tertiary amines, thioethers, sulfoxides, sulfones, disulfide compounds, thioesters, organohalides, and mixtures thereof; and (b) a semiochemical permeable polymeric membrane covering at least a portion of the said polyurethane reservoir and controlling release of the semiochemical from the reservoir, the membrane being selected from the group consisting of polyvinylchloride, polyvinylchloride/vinyl copolymers,low and high density polyethylene, polyethylene/vinyl copolymers, polyethylvinyl acetate and copolymers, polyethylene terpthalate and copolymers, polypropylene, polyamide, polyimide, polyurethane, polyvinylidene fluoride, fluorinated ethylene propylene polymers, polytetrafluoroethylene, silicone rubber, butyl rubber, neoprene rubber, isoprene rubber, cellulose acetate and laminated (co-extruded) membrane types including polyvinylchloride/fluorinated ethylene propylene polymers, polyethylene/ethylvinyl acetate, polyethylene/polyethylene terpthalate.

The semiochemical active ingredient can be selected from the group: E or Z-13-octadecenyl acetate, E or Z-11-hexadecenal, E or Z-9-hexadecenal, hexadecanal, E or Z-11 hexadecenyl acetate,E or Z-9-hexadecenyl acetate, E or Z-11-tetradecenal, E or Z-9-tetradecenal, tetradecanal, E or Z-11-tetradecenyl acetate, E or Z-9-tetradecenyl acetate, E or Z-7-tetradecenyl acetate, E or Z-5-tetradecenyl acetate, E or Z-4-tridecenyl acetate, E or Z-9-dodecenyl acetate, E or Z-8 dodecenyl acetate, E or Z-5-dodecenyl acetate, dodecenyl acetate, 11-dodecenyl acetate, dodecyl acetate, E or Z-7-decenyl acetate, E or Z-5-decenyl acetate, E or Z-3-decenyl acetate, Z or E,Z or E 3,13-octadecadienyl acetate, Z or E, Z or E 2,13-octadecdienyl acetate, Z,Z or E-7,11-hexadecadienyl acetate, Z,E 9,12-tetradecadienyl acetate, E,E-8,10-dodecadienyl acetate, Z,E 6,8-heneicosadien-11-one, E,E 7,9-heneicosadien-11-one, Z-6-henicosen-11-one, 7,8-epoxy-2-methyloctadecane, 2-methyl-7-octadecene, 7,8-epoxyoctadecane, Z,Z,Z-1,3,6,9-nonadecatetraene, 5,11-dimethylheptadecane, 2,5-dimethylheptadecane, 6-ethyl-2,3-dihydro-2-methyl-4H-pyran-4-one, methyl jasmonate, alpha-pinene, beta-pinene, terpinolene, limonene, 3-carene, p-cymene, heptane, ethyl crotonate, myrcene, verbenene, camphene, camphor, cineol, alpha-cubebene, allyl anisole, undecanal, nonanal, heptanal, E-2-hexenal, E-3-hexenal, hexanal, verbenone, 3-methyl-2-cyclohexenone, 3-methyl-3-cyclohexenone, frontalin, exo and endo-brevicomin, lineatin, multistriatin, chalcogran, 7-methyl-1,6-dioxaspiro[4.5]decane, 4,8-dimethyl-4(E),8 (E)-decadienolide, 11-methyl-3 (Z) -undecenolide, Z-3-dodecen-11-olide, Z,Z-3,6-dodecen-11-olide, Z-5-tetradecen-13-olide, Z,Z-5,8-tetradecen-13-olide, Z-14-methyl-8-hexadecenal, 4,8-dimethyldecanal, gamma-caprolactone, hexyl acetate, E-2-hexenyl acetate, butyl-2-methylbutanoate, propylhexanoate, hexylpropanoate, butylhexanoate, hexylbutanoate, butyl butyrate, E-crotylbutyrate, Z-9-tricosene, methyl eugenol, alpha-ionone, 4-(p-hydroxyphenyl)-2-butanone acetate, E-beta-farnasene, nepetalactone, 3-methyl-6-isopropenyl-9-decenyl acetate, Z-3-methyl-6-isopropenyl-3,9-decadienyl acetate, E or Z-3,7-dimethyl-2,7-octadecadienyl propionate, 3-methylene-7-methyl-7-octenyl propionate, 2,6-dimethyl-1,5-heptadien-3-ol acetate, Z-2,2-dimethyl-3-isopropenylcyclobutanemethanol acetate, E-6-isopropyl-3, 9-dimethyl-5,8-decadienyl acetate, Z-5-(1-decenyl)dihydro-2(3H)-furanone, 2-phenethylpropionate, 3,11-dimethyl-2-nonacosanone, 8-methylene-5-(1-methylethyl)spiro|11-oxabicyclo[8.1.0]undecene-2,2-oxiran|-3-one, 2-propylthietane, 3-propyl-1,2-dithiolane, 3,3-dimethyl-1,2-dithiolane, 2,2-dimethylthietane, E or Z-2,4,5-trimethylthiazoline, 2-sec-butyl-2-thiazoline, isopentenyl methyl sulfide.

The active ingredient in composite polymer release devices can be an unnatural synthetic behavior-modifying chemical (semiochemical mimic) as defined above. This group comprises chemicals not found in nature but that cause behaviors that mimic those of a semiochemical.

The semiochemical concentration in the reservoir of a composite polymer controlled release device can be between 0.001% and 80% by weight. The reservoir forming mixture can include substances selected from the group consisting of antioxidants, ultraviolet light absorbers, pigments, dyes, fillers, blowing agents and plasticizers.

The invention in a further aspect is directed to a composite semiochemical controlled release rate dispenser comprising: (a) a cylindrical polyurethane core formed from a polyol, a diisocyanate and an unreactive semiochemical; and (b) a semiochemical permeable rate controlling membrane comprised of a dissimiliar polymeric tubing covering at least a portion of the core.

DRAWINGS

In the drawings, which represent specific embodiments of the invention, but which should not be regarded as restricting the spirit or scope of the invention in any way:

FIG. 3 includes similarly shaped PVC monolithic devices for comparison.

DETAILED DESCRIPTION OF THE INVENTION

The invention consists of versatile composite polymer devices used for dispensing semiochemicals at a controlled rate. Hydroxy-terminated polybutadiene resins and/or other polyols an be combined with additives, semiochemical(s), and an isocyanate component to produce controlled-release reservoirs. By varying the semiochemical load, the cross-linking density of the matrix, the presence of various resin additives, as well as the type of permeable membrane, a variety of release characteristics can be obtained. Semiochemical dispensers can be produced under very mild conditions using a simple process that is readily adapted to automated production of a variety of device forms The main limitation of this method is that the reaction chemistry which forms the device matrix is not compatible with aqueous semiochemical mixtures and semiochemicals that have active hydrogen donating groups.

This technology is an improvement in several aspects of semiochemical dispensers described in prior art. The current technology may be conducted at room temperature and this represents an energy saving over processes using thermal curing (Fitzgerald et al. 1973 and Czechoslovakian Patent No. 8490), melting polymers during semiochemical loading (U.S. Pat. Nos. 4,908,208 and 5,008,115) or radiation curing methods (Kim et al. 1988 and Smith et al. 1991). Moreover, since expensive volatile semiochemicals may be lost during thermal processing, the current technology offers further advantages over this type of prior art.

The invention allows the formation of a semiochemical reservoir in a single step at room temperature. This contrasts strongly with U.S. Pat. Nos. 4,908,208 and 5,008,115 which disclose silicone urethane copolymers which first must be synthesized using inert atmosphere and high temperatures, solvents removed, the copolymer melted and mixed with the with active agent and hot viscous mixture cast into devices. Other prior art membrane bound controlled release devices such as those disclosed in U.S. Pat. No. 4,445,641 also require multiple processing steps. Clearly, the devices specified in the current invention are prepared by a much simpler process.

Other differences between U.S. Pat. Nos. 4,908,208 and 5,008,115 and the current technology are also evident. The subject invention discloses a thermoset polyurethane semiochemical reservoir composed predominately of soft block segments. Prior art silicone urethane copolymers are thermoplastic which require both hard and soft block segments in order to function properly as a controlled release matrix. The urethane component of the copolymers disclosed by Lee and Gornowicz consists of hard block segments derived from short chain polyols and diisocyanates while the soft block component of the are derived from polydiorganosilane and or polyalkylene oxide. Similar silicone urethane copolymers are disclosed as membrane material in U.S. Pat. No. 4,793,555 for the release of aqueous mixtures and this is obviously outside the scope of the subject invention.

Data is presented in U.S. Pat. Nos. 4,908,208 and 5,008,115 that would indicate the practical utility of devices prepared with some of these copolymer active ingredient combinations would be very limited. For example, the release rate data presented in Table II (col. 8 and 9) for active agents in various copolymers is presented as a single value, implying a constant release (zero order kinetics). This is misleading as release kinetics of monolithic devices are known to be logarithmic. Close inspection of release rate data given in Table II (col. 8 and 9) show that 20% trimedlure in copolymer I, 70% trimedlure in copolymer II and 20% glossyplure have release rates higher than the neat chemical. This data appears to be erroneous since it is impossible for inert polymers to increase the vapour pressure of a substance. More importantly, in controlled release applications, the objective is to reduce the release rate from that of the neat chemical to provide sustained release over long periods of time. Obviously these copolymer matricies, at the stated loadings, are not controlling the release of volatile active agents. Similiarly, syneresis is observed with 90% trimedlure in copolymer II (example 5) and 33% benzyl alcohol in copolymer II. This syneresis is an indication of insolubility of volatile agents with the copolymer at this loading level and is a serious dissadvantage in the storage and use of such devices. Clearly, some of these copolymer mixtures appear to be poor release rate regulators for trimedlure, glossyplure and benzyl alcohol. The shortcomings of this technology has limited the use of the devices in semiochemical applications.

The invention is an improvement over prior art monolithic silicone polyurethane copolymer or urethane matrices (U.S. Pat. Nos. 4,908,208, 5,008,115 and 4,594,380). These patents disclose matrix compositions but do not mention nor demonstrate the use of release rate controlling membranes in conjunction with the matrix. In addition, none of these prior art patents indicate that the release rate of any given active agent may be manipulated by changes to the matrix and or the rate controlling membrane. The new composite devices of the invention comprise polyurethane reservoir systems bounded by a dissimilar polymer which acts as a rate controlling membrane. In addition to regulating the release rate, the membrane of the composite devices has further advantages over monolithic devices since it also serves to screen out ultraviolet light and limit exposure to oxygen, both of which may contribute to semiochemical degradation in the matrix.

An example given by Chapin et al. in U.S. Pat. No. 4,594,380 demonstrates the effect of an open container on the release of vapona. This example specifies a monolithic wafer supported in container of unknown composition and geometry with a 950 $mm^2$ opening. There is no permeable membrane to regulate the release characteristics. Furthermore, Chapin et al. at lines 21–27 of column 1, state: "One class of methods comprises dispersion of the active agent throughout (or dissolution in) a substancially inert matrix from which the active agent is gradually released into the environment. The discussion herein will be limited to controlled-release methods of this type, and to devices using this method. Such devices are frequently referred to as 'monolithic' devices." U.S. Pat. No. 4,594,380 therefore pertains to a homogenous, single component (monolithic) device. Clearly, Chapin et al. did not anticipate composite polymer devices using a semi-permeable enveloping membrane of a seperate polymer to regulate the release characteristics.

The teachings of U.S. Pat. No. 4,594,380 are predominately directed to the delivery of toxic agents. It not obvious from these teachings that for many semiochemical uses a very precise delivery of active agent is necessary. U.S. Pat. No. 4,594,380 does not teach that the reactive nature of the urethane curing process may be useful for removal of inhibitors from a semiochemical blend. In addition, no biological or field data demonstrating efficacy was presented by Chapin et al.

The invention has addressed several of the problems inherent in monolithic semiochemical release devices and other prior art devices. The new technology demonstrates that both the reservoir matrix and the device membrane may be membrane may be manipulated. This complimentary combination allows the composite polymer devices better controlled release of semiochemicals than can usually be attained using monolithic devices. Comparisons of the new devices and prior art monolithic dispensers are shown in Examples 1, 3 and 4.

Although the invention as described is not suited to the release of aqueous semiochemical mixtures and semiochemicals with active hydrogen donating groups, this reactivity can be used to purify relatively crude semiochemicals in situ. Impurities of this nature can be trapped by chemical reaction with the isocyanate component during curing of the matrix. This method avoids the need for additional purification of semiochemicals containing low concentrations of impurities with hydroxyl, carboxyl, sulfhydryl and amino functional groups. Example 2 demonstrates this principle.

The physical form of the subject invention can be highly variable. For example, fillers or blowing agents may be included in the formulation to produce a reservoir where a high surface area is desired. Additives may be used to absorb or reflect radiation (pigments, ultraviolet screening agents and carbon black), inhibit oxidation (antioxidants), to increase or decrease the viscosity of the mix and or the release rate of the semiochemical (plasticizers). Devices may be prepared by casting the reactive mixture in polymeric tubing or molds containing the polymer membrane. Layered or laminated devices may also be produced by casting the polyurethane reservoir on various barrier materials or membranes. For example a three layer laminate device might consist of an aluminum foil barrier, polyurethane layer containing the AI and a polyethylene membrane.

Hydroxy-terminated polybutadiene (poly BD™) resins with a range of hydroxyl numbers and molecular weights are available and are preferred components in polymerizing the matrix. Those available from Atochem North America include the following poly BD™ resins: R45M (average molecular weight 2800 and hydroxyl value 0.73 meq/g), R45HT (average molecular weight 2800 and hydroxyl value 0.83 meq/g), R20LM (average molecular weight 1200 and hydroxyl value 1.7 meq/g), and 605 (an epoxidized hydroxyl-terminated polybutadiene with an oxirane content of 6.5% by weight and hydroxyl value of 2.7 meq/g). Poly BD™ resins alone or blended with polyether or polyester polyols are compatible with many classes of semiochemicals. Variation of the mixtures may be used to change the solubility parameter, hydrogen bonding and the extent of cross linking within the matrix by methods known in prior art.

U.S. Pat. No. 4,594,380 has indicated the use of hydroxy or carboxy-terminated copolymers of butadiene and acrylonitrile or styrene as agents to modify a poly BD™ based urethane release matrix. These materials are of high viscosity and are not easily incorporated into the matrix without considerable heating and the use of specialized mechanical mixing equipment. Of far more utility are low viscosity hydroxy-terminated polyethers which may be used to modify the release matrix. Examples of low viscosity polyether polyols compatible with poly BD™ resins include polymers of polyproplene glycol such as Pluracol™ 220 (hydroxyl number 27), Pluracol™ 2010 (molecular weight 2000, hydroxyl number 56) both available from BASF Corporation, and Alkapol™ G-240 (molecular weight 700, hydroxy number 240) available from Rhone-Poulanc Speciality Chemicals, Mississauga, Ontario). Similar materials are available from several other manufacturers. The polyol component can also include materials to enhance the biodegradability of the matrix for example polycaprolactone diol or carbohydrate-based materials (cellulose esters and ethers).

Semiochemical controlled release device reservoirs prepared with a high proportions of hydroxyterminated butadienes will be highly elastic and will consist of predominately of soft block domains. The isocyanate component is generally an MDI with Lupranate™ MM-103 (isocyanate content 29.5% by weight available from BASF Corporation) and Isonate™ 143L (70–80% MDI and 20–30% polymerized MDI, available from Dow Chemical U.S.A.) as examples of suitable commercially available materials. Other isocyanates including toluene diisocyanate, isophorone, diisocyanate and hexamethylene diisocyanate as well as other MDI blends can also be used in the process. The process generally requires no catalysis, however, catalysts known from prior art may be used with some of the slower reacting isocyanate/polyol combinations. Since isocyanates react readily with water, precautions must be taken to insure that the semiochemical, polyol and other matrix additives used are substantially free of water.

The general method for preparation of the polyurethane reservoir is based on the "one shot" batch protocol outlined for the reaction of poly BD™ resins with MDI (Ryan 1971). Typical preparation of a semiochemical reservoir involves warming the polyol component and additives to 35°–75° C. with stirring at a vacuum of 15–100 mm to remove traces of volatile contaminants. The vessel is returned to ambient temperature and pressure and the semiochemical (0–80% w/w) is added to the mix. The mixture is stirred under vacuum until homogeneous. The isocyanate component added (isocyanate index 1.05) and stirring under vacuum continued. The mixture is transferred to molds and left to polymerize. The time for polymerization can vary from a few minutes to several days and is accelerated by catalytic means or by curing at higher temperatures.

The polymeric matrix used for the reservoir is compatible with a large number of semiochemicals. The skilled practitioner will be aware that hundreds of semiochemicals are known and complete listing of compounds compatible with the matrix is clearly impractical. Some examples demonstrating the range of active ingredients suited to incorporation into the composite polymer devices include: lepidopteran pheromones (E or Z-13-octadecenyl acetate, E or Z-11-hexadecenal, E or Z-9-hexadecenal, hexadecanal, E or Z-11 hexadecenyl acetate, E or Z-9-hexadecenyl acetate, E or Z-11-tetradecenal, E or Z-9-tetradecenal, tetradecanal, E or Z-11-tetradecenyl acetate, E or Z-9-tetradecenyl acetate, E or Z-7-tetradecenyl acetate, E or Z-5-tetradecenyl acetate, E or Z-4-tridecenyl acetate, E or Z-9-dodecenyl acetate, E or Z-8 dodecenyl acetate, E or Z-5-dodecenyl acetate, dodecenyl acetate, 11-dodecenyl acetate, dodecyl acetate, E or Z-7-decenyl acetate, E or Z-5-decenyl acetate, E or Z-3-decenyl acetate, Z or E,Z or E 3,13-octadecadienyl acetate, Z or E, Z or E-2,13 octadecadienyl acetate, Z,Z or E-7,11-hexadecadienyl acetate, Z,E 9,12-tetradecadienyl acetate, E,E-8,10-dodecadienyl acetate, Z,E-6,8-heneicosadien-11-one, E,E 7,9-heneicosadien-11-one, Z-6-henicosen-11-one, 7,8-epoxy-2-methyloctadecane, 2-methyl-7-octadecene, 7,8-epoxyoctadecane, Z,Z,Z-1,3,6,9-nonadecatetraene, 5,11-dimethylheptadecane, 2,5-dimethylheptadecane, 6-ethyl-2,3-dihydro-2-methyl-4H-pyran-4-one, methyl jasmonate), bark beetle kairomones (alpha-pinene, beta-pinene, terpinolene, limonene, 3-carene, p-cymene, myrcene, verbenene, camphene, camphor, cineol, alpha-cubebene, allyl anisole, undecanal, nonanal, heptanal, E-2-hexenal, E-3-hexenal, hexanal, heptane, ethyl crotonate), bark beetle pheromones (verbenone, 3-methyl-2-cyclohexenone, 3-methyl-3-cyclohexenone, frontalin, exo and endo-brevicomin, lineatin, multistriatin, chalcogran, 7-methyl-1,6-dioxaspiro[4.5]decane), grain beetle pheromones (4,8-dimethyl-4(E),8(E)-decadienolide, 11-methyl-3 (Z)-undecenolide, Z-3-dodecen-11-olide, Z,Z-3,6-dodecen-11-olide, Z-5-tetradecen-13-olide, Z,Z-5,8-tetradecen-13-olide), dermestid and tenebrionid beetle pheromones (Z-14-methyl-8-hexadecenal, 4,8-dimethyldecanal, gamma-caprolactone), apple maggot kairomones (hexyl acetate, E-2-hexenyl acetate, butyl-2-methylbutanoate, propylhexanoate, hexylpropanoate, butylhexanoate, hexylbutanoate), dipteran pheromones and synthetic attractants (Z-9-tricosene, tert-butyl-4 (or 5)-chloro-2-methyl-cyclohexanecarboxylate, methyl eugenol, alpha-ionone, 4-(p-hydroxyphenyl)-2-butanone acetate) , aphid pheromones (E-beta-farnasene, nepetalactone), hemipteran pheromones (butylbutryate and E-crotylbutryate), homopteran pheromones (3-methyl-6-isopropenyl-9-decenyl acetate, Z-3-methyl-6-isopropenyl-3,9-decadienyl acetate, E or Z-3, 7-dimethyl-2,7-octadecadienyl propionate, 3-methylene-7-methyl-7-octenyl propionate, 2,6-dimethyl-1,5-heptadien-3-ol acetate, Z-2,2-dimethyl-3-isopropenylcyclobutanemethanol acetate, E-6-isopropyl-3, 9-dimethyl-5,8-decadienyl acetate), Japanese beetle pheromone and attractants( Z-5-(1-decenyl)dihydro-2(3H)-furanone, 2-phenethylpropionate), cockroach pheromones (3,11-dimethyl-2-nonacosanone, 8-methylene-5-(1-methylethyl)spiro[11-oxabicyclo[8.1.0]undecene-2,2-oxiran|-3-one), mammal predator kairomones (2-propylthietane, 3-propyl-1,2-dithiolane, 3,3-dimethyl-1, 2-dithiolane, 2,2-dimethylthietane, E or Z-2,4,5-trimethylthiazoline, 2-sec-butyl-2-thiazoline, isopentenyl methyl sulfide). It should be noted that some semiochemicals such as 2,4,5-trimethylthiazoline (with an imine functionality) or tertiary amines, although not reactive (compatible) with the matrix, will act as catalytic agents in the polyurethane forming reaction. These materials are not well suited to the batch method on a large scale, but are easily incorporated in a reaction injection moulding (RIM) process to produce devices.

The presence of a permeable polymer membrane on the dispensers is significant feature of this technology. There are a great number of polymer membrane types commercially available. With this large selection, membrane materials can range from almost impermeable to highly permeable for most semiochemicals. It is recognized that the optimal release rate characteristics will be attained when the membrane material is not a polyurethane composed predominately of hydroxy-terminated polybutadiene. The membrane material may be selected from polyvinyl chloride, PVC/vinyl copolymers, low and high density polyethylene, polyethylene/vinyl copolymers,polyethylvinyl acetate and copolymers, polyethylene terpthalate and copolymers, polypropylene, polyamide, polyimide, polyurethane, polyvinylidene fluoride, fluorinated ethylene proplyene polymers, polytetrafluoroethylene, silicone rubber, butyl rubber, neoprene rubber, isoprene rubber, cellulose acetate and laminated (co-extruded) membrane types (e.g. polyvinylchloride/fluorinated ethylene propylene polymers, polyethylene/ethylvinyl acetate, polyethylene/polyethylene terpthalate and the like).

The composite polymer devices exhibit a characteristic teristic release of semiochemical over time as demonstrated in Examples 1,3, and 5. After manufacture devices are usually stored in vapour tight containers until the dispensers are needed. During this time the semiochemical approaches equilibrium concentrations in the matrix, the surrounding membrane and the atmosphere within the storage container (based on the solubility of the semiochemical in these various media). When these dispensers are removed from storage they will exhibit a moderate to sharp decline in release rate as the semiochemical evaporates from the surface of the device. This drop in release rate takes place over several hours or weeks and depends upon environmental conditions, the volatility of the semiochemical and the type of matrix and membrane combination. Once diffusion of the semiochemical from the matrix to the surface of the membrane has taken place the dispensers will release at more constant levels for prolonged periods. This period of relatively higher release has not hampered the use of these devices in dispensing anti-aggregation pheromones for tree protection or predator kairomones for mammal repellent applications or sex pheromones for mating disruption applications. When dispensers are produced for monitoring traps, they may be removed from storage and "pre-aged" prior to field deployment or the traps simply set out an appropriate time earlier than the anticipated flight of the pest.

A single manufacturing method may be used to produce several different types of release devices using the current invention, exemplified by the casting of the urethane matrix in PVC tubing. Short pieces of tubing (0.2–10.0 cm) can be cut and distributed for ground-based semiochemical dispensers in repellent or mating disruption applications. Similarly, short pieces of the tubing serve as single point source semiochemical emitters used as lures in insect traps. Where point source emitters are not desired, long lengths of semiochemical loaded tubing may be used. For example several meters of loaded tubing may be attached to a tree to provide semiochemical release over a large area. Long lengths of semiochemical-loaded tubing have advantages over devices with small reservoirs in that semiochemical release is possible for extended periods of time. The new technology is capable of producing devices that control the release of AI from minute quantities (ng/day) to a release hundreds of milligrams or even grams of AI per day.

EXAMPLE 1

This example show two similiar but separate experiments demonstrating the effect of a membrane on the release characteristics of the bark beetle anti-aggregation pheromone verbenone from a polyurethane matrix. In these experiments, the matrix was prepared via the basic method outlined that contain verbenone (active ingredient) and a polyurethane composed of poly BD™ R45HT and Lupranate™ MM103. The matrix mixture was divided and used to prepare both composite polymer devices and homogenous monolithic devices in both experiments.

In the first experiment (series A), a mixture containing 9.86% verbenone is allowed to polymerize in PVC tubing (0.5 mm thick and 3.8 mm i.d.) for 16 hours at room temperature in a sealed polyethlene nylon laminate bag. The tubing is cut into 10 cm lengths and in one group of devices, the outer PVC membrane is carefully removed to produce monolithic devices. Each device core contained a calculated load of approximately 100 mg of verbenone.

In the second experiment (series B), a mixture containing 8.96% verbenone is allowed to polymerize in: 1) PVC tubing (0.5 mm thick and 3.0 mm i.d.) which was heat sealed every 10 cm along its length 2) glass tubing 50 cm long×3.0 mm i.d. capped at both ends with a rubber septa. The loaded tubes were left at room temperature in a sealed polyethylene/nylon laminate bag for one week. The loaded PVC tubing was cut every 10 cm at centre of the heat seal to provide composite polymer devices (a urethane core completely surrounded by a permeable PVC membrane). The glass tubes were carefully broken and the resulting urethane rod was cut into 10 cm lengths to provide monolithic (unsheathed) devices. Each device core contained a calculated load of approximately 78 mg of verbenone.

In both experiments, four replicates of the composite polymer devices and four monolithic devices were aged in a temperature controlled environment chamber at 30° for the A series (first experiment) or at 35° C. for the B series (second experiment) with an air flow through the chamber at a rate of 15 cfm. Devices were weighed at regular intervals on a balance with a precision of 0.05 mg. The average cumulative percentage weight loss per device was plotted against time for the first experiment is shown in FIG. 1, A series and the second experiment is shown in FIG. 1, B series.

In both experiments, the effect of the permeable polymer membrane was dramatic, the monolithic devices A and B rapidly lost verbenone such that 50–70% was evaporated in the first 2–3 days. In contrast, the composite polymer devices A and B released verbenone relatively smoothly throughout the test period. After 30 days the monolithic devices had released approximately 85% of the loaded verbenone while the composite devices had released 14–22% of the loaded verbenone. In addition, as demonstrated by the smooth curves, the rate of verbenone release from the composite devices was much more constant than that of the monolithic devices. The composite polymer devices, both A and B, in these experiment were clearly superior in the controlled release of verbenone to the environment over long periods of time.

The two experiments show the similarities between the monolithic devices A and B or the composite devices A and B at both 30° C. and 35° C. There is not much difference between the composite devices A or B. Likewise, the curves for the monolithic devices A and B substancially overlap.

Figure 1:
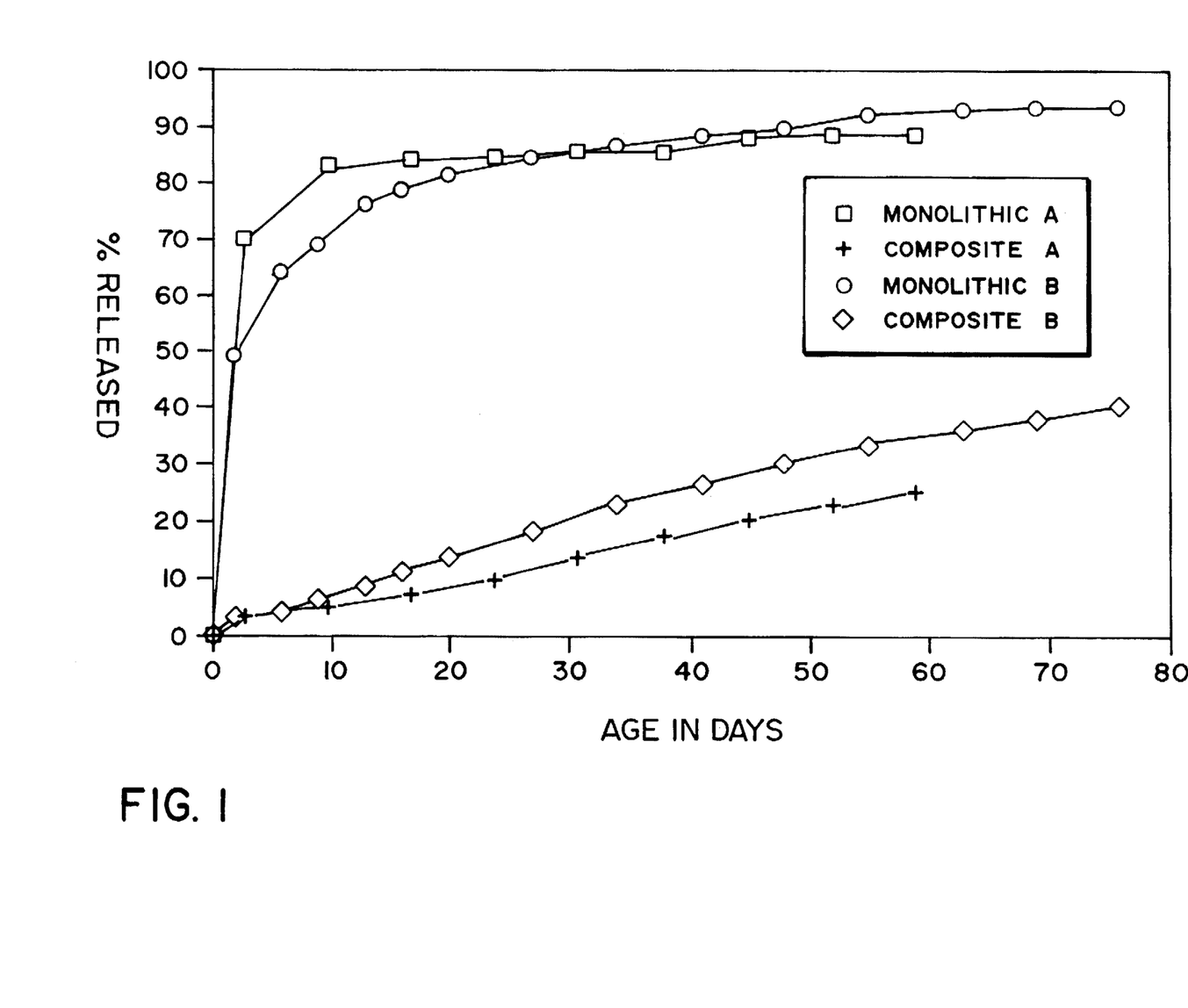
FIG. 1 illustrate graphs which demonstrates cumulative verbenone release from urethane monolithic devices compared with identical urethane cores surrounded by a permeable PVC membrane.

The curves shown in FIG. 1 also demonstrate the permeability of the PVC membrane to verbenone. In the second experiment the composite polymer devices were completely enclosed in the PVC membrane, while in the first experiments the composite polymer devices were open-ended cylinders. In both experiments the effect of the PVC polymer membrane was very clear when compared to the monolithic devices. The release characteristics of both types of composite polymer devices A and B are similar, the effects of the open ends is minimal, even at different temperatures, in comparison to the absence of the membrane. Furthermore, the effects of the open ends is minimized when the geometry of the device is a cylinder many times longer than it is in diameter, as was the case in these experiments.

EXAMPLE 2

This experiment demonstrates the capability of the reservoir forming reaction to purify a crude semiochemical mixture in situ during the curing process. The main component in the pheromone of *Choristoneura fumiferana* is E-11-tetradecenal together with a small percentage of the Z isomer (Silk et al. 1980). The insect response to this pheromone blend is inhibited by E-11-tetradecenol (Sanders 1972) which is often the synthetic precursor to the aldehyde and may be present as a contaminant in some batches of pheromone. A mixture of 34.2 mg of E-11-tetradecenal (92.5% E isomer, 5.3% Z isomer, free of detectable alcohols) and 4.7 mg of E-11-tetradecenol (99% pure) was prepared and a sample subjected to capillary gas chromatography (GC). Under the conditions used, the ratio of peak areas of E-11-tetradecenol to E-11-tetradecenal was 0.1322. Another sample of the aldehyde/alcohol mixture (approximately 2.0% w/w) was polymerized with 20% w/w of dioctyladipate and poly BD™ R45HT and Lupranate™ MM 103 (isocyanate index 1.1). After polymerization the resulting plug was loosened from the vial walls and extracted with five volumes of hexanes overnight. A sample of the extract was diluted six fold and subjected again to GC analysis. After this analysis the ratio of peak areas of E-11-tetradecenol to E-11-tetradecenal was now 0.0049. The results demonstrate that approximately 96% of the original E-11-tetradecenol had been removed during the curing process. This example also serves to demonstrate why semiochemicals with active hydrogen donating groups are not compatible with this type of polyurethane reservoir.

EXAMPLE 3

Figure 2:
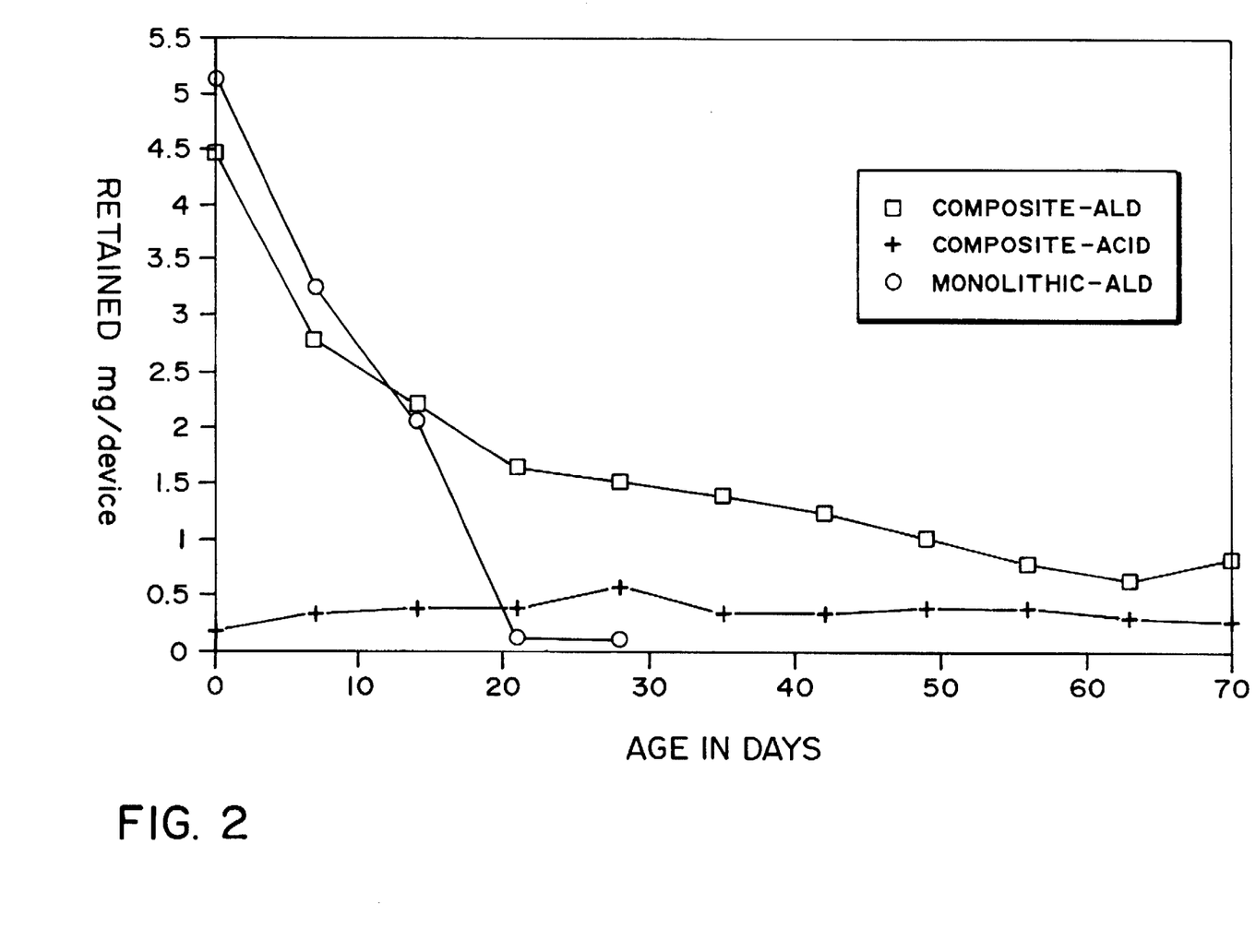
FIG. 2 illustrates a graph of average retained Z-11-hexadecenal residue per device aged in a Florida cotton field as a function over time.

This example demonstrates that the composite polymer devices have sustained release capabilities for a labile lepidopteran pheromone. The new dispensers are compared with prior art monolithic devices. A polymeric core formulated from poly BD™ R45HT, Isonate™™ 143 L, 14.5% dioctyladipate w/w and 1.37% Z-11-hexadecenal w/w as the active ingredient AI was cast into PVC tubing 4.8 mm diameter with 0.5 mm wall thickness. Cylinders 42 mm long were cut from the tubing to form the devices used in this test. Devices were tethered to cotton plants and exposed to ambient conditions in Florida during August–October 1991. Sample devices were collected at weekly intervals, sealed in nylon polyethylene laminate bags and stored at 5° C. or lower until analysis. Samples consisting of three devices were repeatedly extracted with hexanes, the extracts were pooled, treated with Hexadecane as an internal standard and analyzed by capillary column gas chromatography. The extracts were analyzed for AI and Z-11-Hexadecenoic acid, an expected oxidation product of the AI. The results of the residue analysis are graphed as a function over time in FIG. 2. Results from similarly shaped PVC monolithic devices are included for comparison in FIG. 2. Clearly, the composite polymer devices have superior controlled release properties when compared to the monolithic devices. The results demonstrate that the composite polymer device affords some protection of the pheromone from oxidation. Except for an initial sharp drop in the residue weights in the first two weeks, the devices exhibit a smooth release of AI for over 60 days under relatively high temperature field conditions. Such a device is potentially useful for mating disruption of Heliocoverpa (Heliothis) species.

EXAMPLE 4

In this example, composite polymer lures were compared with two types of monolithic PVC lures in sticky traps. The biological assay was conducted at sites in Oregon, Washington, California and Idaho in 1991. The devices were 4 mm diameter with a wall thickness of 0.5 mm with a core composition containing poly BD™ R45HT, Isonate™ 143L, 50% w/w dioctyladipate and 0.001 % w/w of Z-6-Henicosen-11-one as AI. The PVC devices were 5 mm long and the urethane cored devices were 8 mm long, with all devices containing equivalent weights (approximately 500 ng each) of AI. The results of this test are shown in Table 1.

TABLE 1

| Summary of Douglas-Fir tussock moth lure evaluation. | | | |
|---|---|---|---|
| Lure Type | PVC 1 | PVC 2 | COMPOSITE |
| # of sites (4 blocks/site) | 27 | 27 | 27 |
| Sum of avg # insects trapped/block | 414.92 | 596.00 | 685.83 |
| Avg # insects trapped/block | 15.37 | 22.07 | 25.40 |
| Standard Deviation | 23.63 | 23.71 | 24.66 |
| Maximum # trapped/block | 87.50 | 81.75 | 75.75 |

The results demonstrate that composite polymer devices show good biological activity and no inhibitors of the biological response were present. These devices are useful as an early warning monitoring tool for detecting Douglas-Fir tussock moth populations.

EXAMPLE 5

Figure 3:
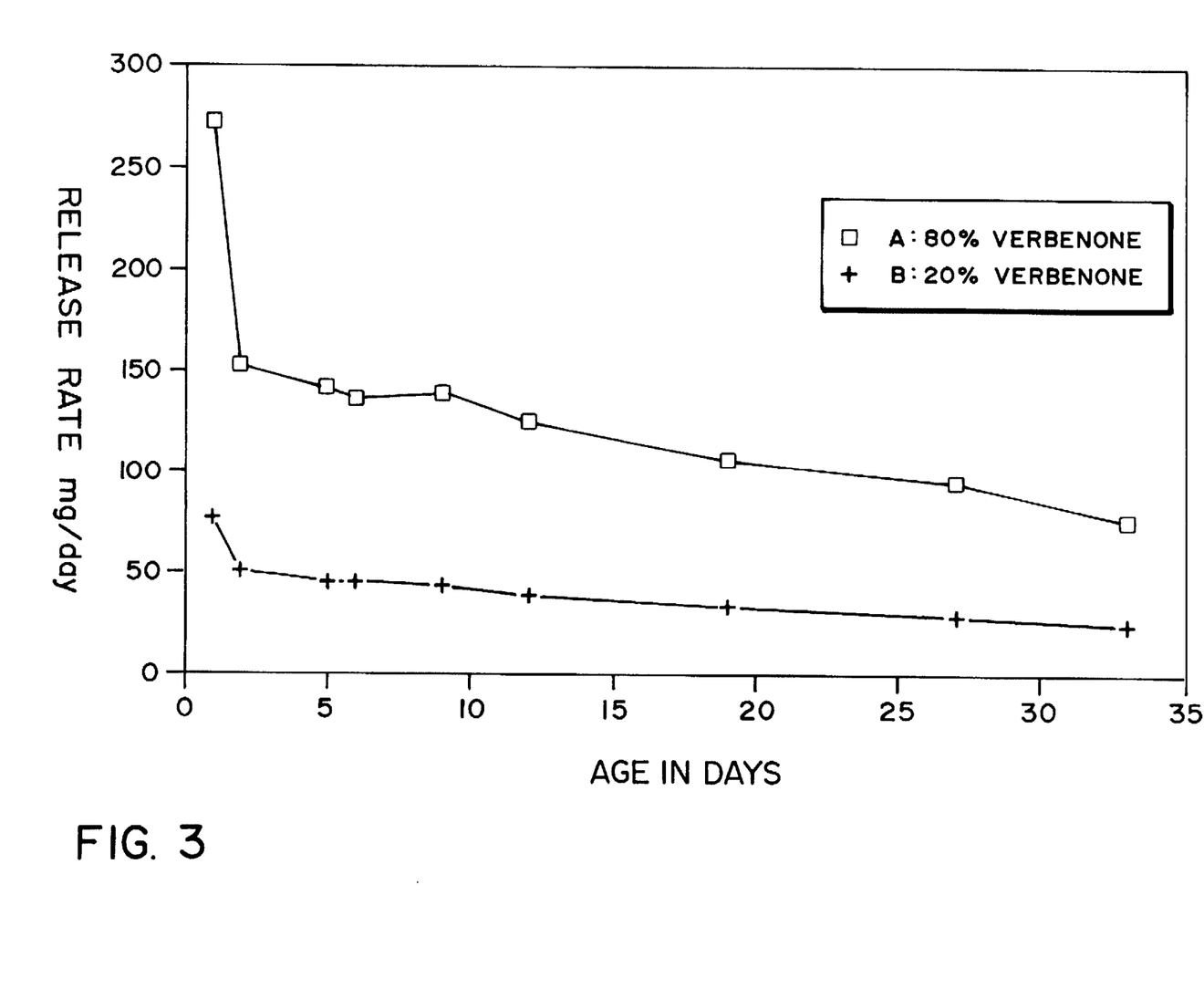
FIG. 3 illustrates a plot of mean release rate (mg/hour/device) of verbenone from composite polymer release devices according to the invention, as a function of time.

In this example two different urethane semiochemical blends were cast into lengths of ethylvinyl acetate/ethylene copolymer tube stock 12 micron thick to produce pouches 5.2×10.0 cm. After loading with semiochemical and polymer, the packages were heat sealed and allowed to polymerize. The composite polymer devices were made to contain 5.0 g each of verbenone as the semiochemical. Sample A devices contained 80% verbenone w/w and 20% polyurethane prepared from poly BD™ R45-HT and Lupranate™ MM-103. Sample B devices contained 20% verbenone w/w and 80% polyurethane prepared from poly BD™ R20LM and lupranate™ MM-103. The devices were aged in a temperature controlled chamber at 24° C. with a flow of air through the chamber of 15 cfm. Release rate of semiochemical from the controlled devices was determined by weight loss. The observed mean release of verbenone from these devices over time is shown in FIG. 3. The results demonstrate that resin type and pheromone load can substantially alter the release rate characteristics of these devices. Devices such as these are useful for dispensing anti-aggregation pheromones of bark beetles.

EXAMPLE 6

Many different composite polymer devices have been used to deliver semiochemicals under conditions of actual field use. The type of membranes used has included polyvinyl chloride, PVC/vinyl copolymers, low and high density polyethylene, polypropylene, nylon, polyethylene/vinyl copolymers, polyethylvinyl acetate and copolymers, polypropylene, nylon (polyamide), and laminated (coextruded) polyethylene/nylon. The types of semiochemicals has included: Z-11-hexadecenal, Z-9-hexadecenal, E-11-tetradecenal, Z-9-tetradecenal, E or Z-11-tetradecenyl acetate, E and Z-9-dodecenyl acetate, Z-7-decenylacetate, Z,E 9,12-tetradecadienyl acetate, Z,E 6,8-heneicosadien-11-one, E,E 7,9-heneicosadien-11-one, Z-6-henicosen-11-one, 7,8-epoxy-2-methyloctadecane, 2-methyl-7-octadecene, 7,8-epoxyoctadecane, alpha-pinene, terpinolene, limonene, 3-carene, p-cymene, heptane, allyl anisole, undecanal, nonanal, hexanal, verbenone, frontalin, exobrevicomin, conophthorin (7-methyl-1,6-dioxaspiro[4.5]decane), Z-14-methyl-8-hexadecenal, hexyl acetate, E-2-hexenyl acetate, butyl-2-methylbutanoate, propylhexanoate, hexylpropanoate, butylhexanoate, hexylbutanoate), butylbutrate, E-crotylbutyrate, Z-9-tricosene, 2-propylthietane, 3-propyl-1,2-dithiolane, 2,2-dimethylthietane, E and Z-2,4,5-trimethylthiazoline, and isopentenyl methyl sulfide).

As will be apparent to those skilled in the art in the light of the foregoing disclosure, many alterations and modifications are possible in the practice of this invention without departing from the spirit or scope thereof. Accordingly, the scope of this invention is to be construed in accordance with the substance defined by the following claims.

What is claimed is:

1. A composite polymer semiochemical controlled release dispenser comprising:
   (a) a cylindrical polyurethane reservoir formed in one-reaction step from a reaction mixture of
      (i) a polyol selected from the group consisting of hydroxy-terminated polybutadiene resins, hydroxy-terminated polyether resins, and hydroxy-terminated polyester resins; and
      (ii) an isocyanate selected from the group consisting of monomeric or polymeric diphenylmethane diisocyanate, toluene diisocyanate, isophorone diisocyanate, hexamethylene diisocyanate and polymeric hexamethylene diisocyanate; and as non-reactive active ingredient
      (iii) a semiochemical which is unreactive with the polyol and isocyanate, said semiochemical being selected from the group consisting of alkanes, alkenes, alkynes, aromatic hydrocarbons, ethers, esters, epoxides, aldehydes, ketones, lactones, nitriles, imines, tertiary amines, thioethers, sulfoxides, sulfones, disulfide compounds, thioesters, organohalides, and mixtures thereof, and which semiochemical is compatible with the polyol and isocyanate and does not lose its semiochemical properties; and
   (b) a tubular semiochemical permeable polymeric membrane covering the circumferential surface of the cylindrical polyurethane reservoir and regulating the release of the semiochemical from the reservoir, said membrane being selected from the group consisting of polyvinylchloride, polyvinylchloride/polyvinyl copolymers, low and high density polyethylene, polyethylene/polyvinyl copolymers, polyethylvinyl acetate and copolymers thereof, polyethylene terpthalate and copolymers thereof, polypropylene, polyamide, polyimide, polyurethane, polyvinylidene fluoride, fluorinated ethylene propylene polymers, polytetrafluoroethylene, silicone rubber, butyl rubber, neoprene rubber, isoprene rubber, cellulose acetate and laminated (co-extruded) membranes comprising polyvinylchloride/fluorinated ethylene propylene polymers, polyethylene/ethylvinyl acetate, and polyethylene/polyethylene terpthalate, said polymeric tubing being of a substance which has a semiochemical permeability which is different from the semiochemical permeability of the polyurethane reservoir.

2. A composite polymer semiochemical controlled release dispenser according to claim 1 wherein the reservoir forming mixture includes substances selected from the group consisting of anti-oxidants, ultraviolet light absorbers, pigments, dyes, fillers, blowing agents, and plasticizers.

3. A composite polymer semiochemical controlled release dispenser according to claim 1 wherein the semiochemical concentration in the said reservoir is between 0.001% and 80% by weight of the reservoir.

4. A composite polymer controlled release dispenser according to claim 1 wherein the active ingredient is an insect behaviour-modifying semiochemical mimic.

5. A composite polymer controlled release dispenser according to claim 2 wherein the active ingredient is an insect behaviour-modifying semiochemical mimic.

6. A composite polymer controlled release dispenser according to claim 3 wherein the active ingredient is an insect behaviour-modifying semiochemical mimic.

7. A composite polymer semiochemical controlled release dispenser comprising:
   (a) a cylindrical polyurethane reservoir formed from a reaction mixture of
      (i) a polyol selected from the group consisting of hydroxy-terminated polybutadiene resins, hydroxy-terminated polyether resins, and hydroxy-terminated polyester resins; and
      (ii) an isocyanate selected from the group consisting of monomeric or polymeric diphenylmethane diisocyanate, toluene diisocyanate, isophorone diisocyanate,hexamethylene diisocyanate and polymeric hexamethylene diisocyanate; and as a non-reactive active ingredient (iii) a semiochemical which is unreactive with the polyol and isocyanate, said semiochemical being selected from the group consisting of E or Z-13-octadecenyl acetate, E or Z-11-hexadecenal, E or Z-9-hexadecenal, hexadecanal, E or Z-11 hexadecenyl acetate, E or Z-9-hexadecenyl acetate, E or Z-11-tetradecenal, E or Z-9-tetradecenal, tetradecanal, E or Z-11-tetradecenyl acetate, E or Z-9-tetradecenyl acetate, E or Z-7-tetradecenyl acetate, E or Z-5-tetradecenyl acetate, E or Z-4-tridecenyl acetate, E or Z-9-dodecenyl acetate, E or Z-8 dodecenyl acetate, E or Z-5-dodecenyl acetate, dodecenyl acetate, 11-dodecenyl acetate, dodecyl acetate, E or Z-7-decenyl acetate, E or Z-5-decenyl acetate, E or Z-3-decenyl acetate, Z or E,Z or E 3,13-octadecadienyl acetate, Z or E, Z or E2,13-octadecdienyl acetate, Z,Z or E-7,11-hexadecadienyl acetate, Z,E9,12-tetradecadienyl acetate, E,E-8,10-dodecadienyl acetate, Z,E 6,8-heneicosadien-11-one, E,E 7,9-heneicosadien-11-one, Z-6-henicosen-11-one, 7,8-epoxy-2-methyloctadecane, 2-methyl-7-octadecene, 7,8-epoxyoctadecane, Z,Z,Z-1,3,6,9-nonadecatetraene, 5,11-dimethylheptadecane,2,5-dimethylheptadecane,6-ethyl-2,3-dihydro-2-methyl-4H-pyran-4-one, methyl jasmonate, alpha-pinene, beta-pinene, terpinolene, limonene, 3-carene, p-cymene, heptane, ethyl crotonate, myrcene, verbenene, camphene, camphor, cineol, alpha-cubebene, allyl anisole, undecanal, nonanal, heptanal, E-2-hexenal, E-3-hexenal, hexanal, verbenone, 3-methyl-2-cyclohexenone, 3-methyl-3-cyclohexenone, frontalin, exo and endobrevicomin, lineatin, multistriatin, chalcogran, 7-methyl-1,6-dioxaspiro[4.5]decane,4,8-dimethyl-4(E),8(E)-decadienolide,11-methyl-3(Z)-undecenolide, Z-3-dodecen-11-olide,Z,Z-3,6-dodecen-11-olide,Z-5-tetradecen-13-olide, Z,Z-5,8-tetradecen-13-olide, Z-14-methyl-8-hexadecenal, 4,8-dimethyldecanal, gamma-caprolactone, hexyl acetate, E-2-hexenyl acetate, butyl-2-methylbutanoate, propylhexanoate, hexylpropanoate, butylhexanoate, hexylbutanoate, butyl butyrate, E-crotylbutyrate, Z-9-tricosene, methyl eugenol, alpha-ionone, 4-(p-hydroxyphenyl)-2-butanone acetate, E-beta-farnasene, nepetalactone, 3-methyl-6-isopropenyl-9-decenyl acetate, Z-3-methyl-6-isopropenyl-3,9-decadienyl acetate, E or Z-3,7-dimethyl-2,7-octadecadienyl propionate, 3-methylene-7-methyl-7-octenyl propionate, 2,6-dimethyl-1,5-heptadien-3-ol acetate, Z-2,2-dimethyl-3-isopropenylcyclobutanemethanol acetate, E-6-isopropyl-3,9-dimethyl-5,8-decadienyl acetate, Z-5-(1-decenyl)dihydro-2(3H)-furanone, 2-phenethylpropionate, 3,11-dimethyl-2-nonacosanone, 8-methylene-5-(1-methylethyl)spiro [11-oxabicyclo[8.1.0]undecene-2,2-oxiran]-3-one, 2-propylthietane, 3-propyl-1,2-dithiolane, 3,3-dimethyl-1,2-dithiolane, 2,2-dimethylthietane, E or Z-2,4,5-trimethylthiazoline, 2-sec-butyl-2-thiazoline, and isopentenyl methyl sulfide; and (b) a surrounding tubular semiochemical permeable polymeric membrane covering the circumference of the polyurethane reservoir and controlling the release of the semiochemical from the reservoir, said membrane being selected from the group consisting of polyvinylchloride, polyvinylchloride/vinyl copolymers, low and high density polyethylene, polyethylene/polyvinyl copolymers, polyethylvinyl acetate and copolymers thereof, polyethylene terpthalate and copolymers thereof, polypropylene, polyamide, polyimide, polyurethane, polyvinylidene fluoride, polyfluorinated ethylene propylene, polytetrafluoroethylene, silicone rubber, butyl rubber, neoprene rubber, isoprene rubber, cellulose acetate and laminated, co-extruded, membranes of polyvinylchloride/fluorinated ethylene propylene, polyethylene/ethylvinyl acetate, and polyethylene/polyethylene terpthalate, said polymeric membrane being of a substance which has a semiochemical permeability which is different from the semiochemical permeability of the polyurethane reservoir.

* * * * *